US010462382B2

(12) United States Patent
Robert et al.

(10) Patent No.: US 10,462,382 B2
(45) Date of Patent: Oct. 29, 2019

(54) SINGLE-MODALITY-BASED VISUAL DISTINGUISHING OF MEDICAL INTERVENTION DEVICE FROM TISSUE

(71) Applicant: KONINKLIJKE PHILIPS N.V., Eindhoven (NL)

(72) Inventors: Jean-luc Robert, Cambridge, MA (US); Emil George Radulescu, Ossining, NY (US); Richard Allen Snyder, Chester, NH (US); Sanghamithra Korukonda, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 28 days.

(21) Appl. No.: 15/534,038

(22) PCT Filed: Dec. 1, 2015

(86) PCT No.: PCT/IB2015/059231
§ 371 (c)(1),
(2) Date: Jun. 8, 2017

(87) PCT Pub. No.: WO2016/092415
PCT Pub. Date: Jun. 16, 2016

(65) Prior Publication Data
US 2017/0366756 A1    Dec. 21, 2017

Related U.S. Application Data

(60) Provisional application No. 62/254,260, filed on Nov. 12, 2015, provisional application No. 62/089,470, filed on Dec. 9, 2014.

(51) Int. Cl.
*H04N 5/265* (2006.01)
*G06T 7/00* (2017.01)
(Continued)

(52) U.S. Cl.
CPC .......... *H04N 5/265* (2013.01); *A61B 8/0841* (2013.01); *A61B 8/463* (2013.01); *A61B 8/5246* (2013.01);
(Continued)

(58) Field of Classification Search
CPC combination set(s) only.
See application file for complete search history.

(56) References Cited

U.S. PATENT DOCUMENTS 6,733,458 B1    5/2004   Steins et al.
8,509,508 B2    8/2013   Choi et al.
(Continued)

OTHER PUBLICATIONS

Bamber, Jeffrey C., "Image Formation and Image Processing in Ultrasound", Joint Department of Physics, Institute of Cancer Research and The Royal Marsden NHS Trust, 1999.

*Primary Examiner* — Alexander Gee
(74) *Attorney, Agent, or Firm* — Sherry Austin

(57) ABSTRACT

Depiction, within a single imaging modality, of an intervention device and body tissue surrounding the device, is improved by interrogating a subject that includes the intervention device and the tissue. An image is created using, for a parameter, a value, of the parameter (160), better suited to one or the other of a device region depicting the intervention device and a tissue region depicting the tissue. The value is used to yield respectively either a first image (152) or a second image (154). Respective presets may correspondingly have different values for the parameter. From jointly the first image and the second image which are both of the single modality, a combination is formed that is an image of the intervention device depicted as surrounded by the tissue. The combinations may be formed dynamically and ongoingly. An apparatus for the improved depiction may be configured for the use of the parameter in a stage prior to (Continued)

image processing conducted on a scan-converted image (146) if such image processing is employed.

20 Claims, 3 Drawing Sheets

(51) Int. Cl.
| | | |
|---|---|---|
| *G06T 7/11* | (2017.01) | |
| *A61B 8/08* | (2006.01) | |
| *A61B 8/00* | (2006.01) | |
| *G01S 15/89* | (2006.01) | |
| *G01S 7/52* | (2006.01) | |
| *A61B 8/12* | (2006.01) | |

(52) U.S. Cl.
CPC .............. *A61B 8/54* (2013.01); *G06T 7/0012* (2013.01); *G06T 7/11* (2017.01); *A61B 8/0883* (2013.01); *A61B 8/12* (2013.01); *A61B 8/467* (2013.01); *G01S 7/52074* (2013.01); *G01S 15/8995* (2013.01); *G06T 2207/10132* (2013.01); *G06T 2207/30024* (2013.01)

(56) References Cited

U.S. PATENT DOCUMENTS

| | | | |
|---|---|---|---|
| 8,858,436 | B2 | 10/2014 | Pagoulatos et al. |
| 2002/0173719 | A1* | 11/2002 | Zhao .................... A61B 8/0833 600/437 |
| 2004/0002653 | A1* | 1/2004 | Greppi ..................... A61B 8/06 600/439 |
| 2004/0006266 | A1* | 1/2004 | Ustuner ................... A61B 8/08 600/407 |
| 2009/0247873 | A1 | 10/2009 | Kondo |
| 2010/0160780 | A1* | 6/2010 | Swan ................ A61B 5/02007 600/439 |
| 2011/0249878 | A1* | 10/2011 | Pagoulatos .......... A61B 8/0841 382/131 |
| 2013/0184580 | A1* | 7/2013 | Lause ................ G01S 7/52066 600/440 |
| 2013/0345566 | A1 | 12/2013 | Weitzel et al. |
| 2014/0121502 | A1 | 5/2014 | Vignon et al. |
| 2014/0187948 | A1 | 7/2014 | Gerard et al. |

\* cited by examiner

SINGLE-MODALITY-BASED VISUAL DISTINGUISHING OF MEDICAL INTERVENTION DEVICE FROM TISSUE

This application is the U.S. National Phase application under 35 U.S.C. § 371 of International Application No. PCT/IB2015/059231, filed on Dec. 1, 2015, which claims the benefit of both U.S. Provisional Application Ser. No. 62/254,260, filed Nov. 12, 2015 and U.S. Provisional Application Ser. No. 62/089,470, filed Dec. 9, 2014. These applications are hereby incorporated by reference herein.

FIELD OF THE INVENTION

The present invention relates to enhancing an image of an intervention device surrounded by body tissue and, more particularly, to doing so selectively as to device or tissue region.

BACKGROUND OF THE INVENTION

Ultrasound systems are typically equipped with presets. Each one is a set of imaging parameters and values for the parameters. As part of system initialization, the set is fed to an algorithm for optimizing visualization in a particular type of ultrasound examination. A group of user-selectable icons, each representing a preset, may be shown onscreen. A system with presets provided by the manufacturer, user-designation, or user experience is disclosed in U.S. Pat. No. 8,509,508 to Choi et al.

One of the limitations of ultrasound imaging for mitral valve replacement is poor visualisation of the mitral valve clip. One artifact is the so called "ringing" artifact. Devices are usually much more reflective than tissue, and metal parts tend to produce reverberations. As a result, the preset is typically not adapted to device visualization. Thus, devices often appear with very high, often saturated, intensity. Enhanced side lobes and reverberations make it difficult to visualize the device position and edges. Because of the poor resolution and strong reverberation in imaging the clip, it is difficult for the user to know exactly where the clip is and to position it accurately.

When a lower gain or mechanical index (MI), or a smaller dynamic range, is used, the reverberation and side lobes of the device are much less visible, leading to a better visualisation. However, in that case the tissue is no longer visualized properly.

SUMMARY OF THE INVENTION

What is proposed herein below is directed to addressing one or more of the above-discussed concerns.

There exists a need for better visualization of the clip and clear definition of its edges when it is inserted through the valve.

In an aspect of what is proposed herein below, an imaging apparatus is configured for improved depiction, within a single imaging modality, of an intervention device and body tissue surrounding the device.

The apparatus includes image acquisition and formation circuitry configured for interrogating a subject that includes the intervention device and the tissue. An image is created using, for a parameter, a value, of the parameter, better suited to one or the other of a device region depicting the intervention device and a tissue region depicting the tissue. The value is used to yield respectively either a first image or a second image.

The apparatus also includes image combination circuitry configured for forming, jointly from the first image and the second image which are both of the single modality, a combination that is an image of the intervention device depicted as surrounded by the tissue.

The apparatus also includes control circuitry configured for dynamically invoking the image acquisition and forming and image combination circuitry to dynamically produce, via the joint forming, combinations.

A related method entails interrogating, via emission and receipt of energy, a subject that includes the intervention device and the tissue. Via a processor, an image is created using, for a parameter, a value, of the parameter, better suited to one or the other of a device region depicting the intervention device and a tissue region depicting the tissue. The value is used to yield respectively either a first image or a second image. The processor has a pipeline having stages. For respectively the first or the second image, and if image processing is conducted on a scan-converted image, the using of the value occurs at a stage prior to such image processing.

A related computer readable medium embodies a program for medical imaging that affords improved depiction, within a single medical imaging modality, of an intervention device and body tissue surrounding the intervention device. The medium has instructions executable by a processor for performing a plurality of acts. Included among the acts are: using, for a parameter, a parameter value better suited to one or the other of a device region depicting the intervention device and a tissue region depicting the tissue, to yield respectively either a first image or a second image. Also included is dynamically performing repeatedly the using to yield first and second images so as to pair first and second images which are both of that same modality and dynamically forming repeatedly, from the pairs, combinations that are each an image of the intervention device depicted as surrounded by the tissue.

Details of the region-specific imaging for overall visual enhancement are set forth further below, with the aid of the following drawings, which are not drawn to scale.

DETAILED DESCRIPTION OF EMBODIMENTS

Figure 1:
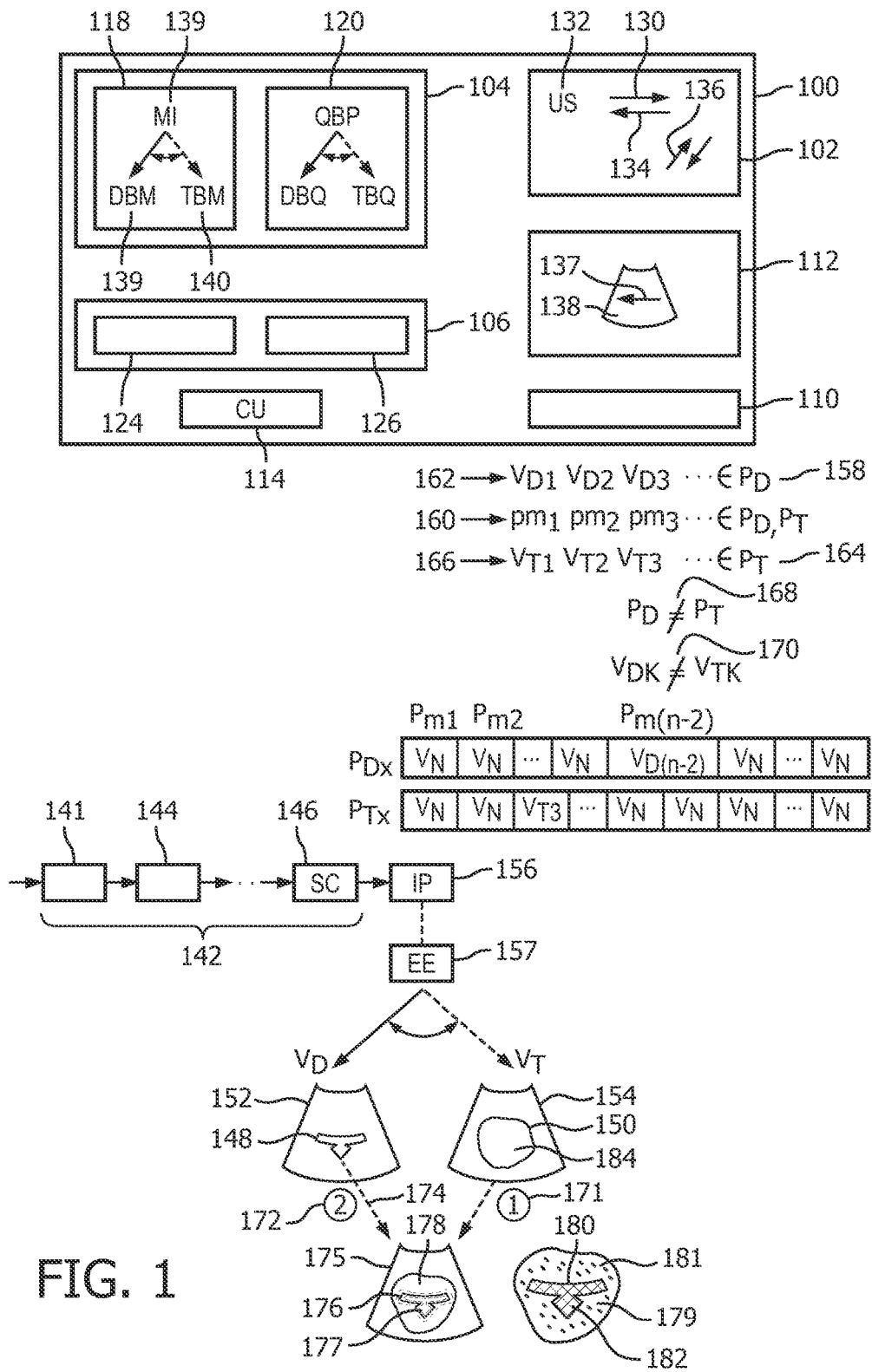
FIG. 1 is a schematic and conceptual diagram exemplary of region-specific imaging for overall visual enhancement in accordance with the present invention.

FIG. 1 shows, by way of illustrative and non-limitative example, a region-specific imaging apparatus 100 for overall visual enhancement. The apparatus 100 includes an ultrasound probe 102, image acquisition and formation circuitry 104, image combination circuitry 106, user controls 110, a display 112, and control circuitry 114.

As the term is used herein, circuitry includes not only computer circuits, but either software and data that control the circuits, or hardware and/or firmware that are functionally equivalent to the software and data. Thus, "circuitry" may refer to a computer memory circuit in combination with the data and program instructions held by the circuit. Accordingly, the "image acquisition and formation circuitry" 104 is implementable as a medical imaging acquisition unit 118 and a medical imaging post-processing unit 120. The "image combination circuitry" 106 may include a medical-image segmentation unit 124 and a medical-image overlay module 126. A control unit, as the "control circuitry" 114, may operate the image acquisition and formation circuitry 104 and the image combination circuitry 106. These three circuitries 104, 106, 114 can be physically separate or to some extent physically overlapping.

The probe 102 emits 130 ultrasound 132 and receives 134 the echoed-back ultrasound. The ultrasound interrogation will generally occur through an acoustic window used by the probe 102 in the current examination. The probe 102 may be a transesophageal echocardiography ("TEE") or transthoracic echocardiography ("TTE") probe. Optionally, two or more acoustic windows may be used. They can be used alternately, for example interrogating through one window and then through the other. Thus, the same region of interest ("ROI") can be interrogated through one acoustic window and then, for instance from a different direction 136, from a second acoustic window. One interrogation could be optimized to an intervention device 137, the other, possibly through a different acoustic window, being optimized to the surrounding body tissue 138. The separate acoustic windows could be provided by the same probe, separate probes, or by a single probe having a large surface area such as a large area transthoracic echocardiography ("LATTE") probe. An example of a LATTE probe is provided in International Patent Publication No. WO2105/087191 to Korukonda et al. The results of the two interrogations are combined to form an image that has been enhanced overall. As shown conceptually in FIG. 1 on the display 112 at something close to a transthoracic angle, a mitral valve clip is the intervention device 137. The clip has wings emanating from what is seen in FIG. 1 as the point of the arrowhead, the wings being in an unextended position.

Both the emission and the reception of the ultrasound are accomplished using associated imaging parameters having respective values. The subsequent post-processing, and any further image processing, also entail the use of associated imaging parameters having respective values.

In some implementations, the apparatus 100, during interrogation, toggles back and forth between two transmit modes. They may use different wavefronts, central frequencies, beam densities, mechanical index (MI), analog gain, or differ as to other parameter values. For example, as the intervention device 137 is more reflective than the body tissue 138 that surrounds the device, it will be less affected by attenuation. This is significant because raising the frequency lowers the imaging depth observable with a given signal strength; however, since observation of the device is less affected by attenuation, the signal strength can be lower if the device is what we are interested in observing, even given the fact that the device and the tissue are at essentially the same imaging depth. Thus, for observing the device, we can raise the frequency, which yields a better resolution to the device. Higher beam density will also improve device resolution. A lower MI or analog gain is also suitable for the device. An imaging acquisition parameter MI 139, for instance, can be provided with a device-based value DBM 139 in one transmit mode, and a different, i.e., tissue-based, value TBM 140 in another transmit mode. The two thus different transmit modes are defined by two correspondingly different sets of imaging parameter values in what are therefore two different presets. One of the two presets is used to yield a device based image and the other is used to yield a tissue based image (i.e., images yielded using respectively the device-enhancing or tissue-enhancing parameter value), which will be referred to hereinafter as the "first image" and the "second image." The designations "first" image and "second" image are not meant to imply an ordering of the first and second images.

It is also possible for the same acquisition to be used for yielding the first and second images, if different post-processing parameters are used. Examples are digital gain, compression, gamma correction, quadrature bandpass (QBP) filter coefficients, and intensity based thresholding. As to compression, a lower dynamic range could be used for the device, for example 30 dB versus 50 for the tissue. Reduced digital gain could also be used for the device. This post-processing embodiment yields good results if the signal corresponding to the device is not so saturated that it is clipped during analog-to-digital (A/D) conversion.

Likewise, the parameters for the first and second images can vary both as to acquisition parameters and post-processing parameters.

The image acquisition and formation circuitry 104 has, with respect to a given frame of image data, a pipeline 141 that includes a set 142 of stages 144. Some examples of the stages 144 are pulse-echo acquisition, completion of beam-forming, completion of scan conversion, and possibly edge detection.

Edge detection can be a form of image processing conducted on an image 146 that has already undergone, and is therefore the output of, scan conversion.

Such edge detection is, according to some embodiments of what is proposed herein, pipeline-wise beyond the set 142 of stages 144 for which a parameter more suited, in terms of visualization, to a device region 148 than to a tissue region 150, or vice versa, is potentially used to create a first image 152 or second image 154. The first and second images 152, 154 are a pair to be combined, as discussed further below. The depiction in FIG. 1 of the mitral valve clip with the reference numeral 148 shows the clip at a TEE angle with its wings extended. Although in FIG. 1 the first image 154 does not show any surrounding body tissue, an actual first image would generally show some tissue but with poor visualization.

More generally and according to what is proposed herein, using, for some embodiments, a parameter value more suited to one of the two regions 148, 150 to create respectively the first or second image 152, 154 occurs in a stage 144 prior to image processing 156 conducted on a scan-converted image 146 if such image processing is employed. Examples of such image processing 156 are edge enhancement 157 and smart image processing.

A first preset 158 is made up of a set 160 of parameters pm1, pm2 . . . and of a respective set of values 162 $V_{D1}$, $V_{D2}$ . . . . At least one of the values 162 is better suited to the device region 148 than to the tissue region 150.

A second preset 164 is made up of the same set 160 of parameters pm1, pm2 . . . and of a respective set of values 166 $V_{T1}$, $V_{T2}$ . . . . At least one of the values 166 is better suited to the tissue region 150 than to the device region 148.

The first preset 158 is consequently different 168 from the second preset 164.

Typically, too, for some k, $V_{Dk}$ is different 170 from $V_{Tk}$.

Thus, for example, if the parameter is dynamic range, 30 dB may be used for the first image 152 and 50 dB used for the second image 154.

However, it is not necessary that $V_{Dk}$ be different 170 from $V_{Tk}$ for some k.

For example, for at least some parameter of the set 160, a value could exist that is neither suited to the device region 148 nor to the tissue region 150, e.g., a value $V_N$ that is numerically intermediate. Thus, with a value $V_{D(n-2)}$ better suited to the device region 148 and a value $V_{T3}$ better suited to the tissue region 150, it still is the case that the two respective presets $P_{Dx}$ and $P_{Tx}$ differ, and that the presets are applicable in respectively yielding the first and second images 152, 154.

According to some embodiments, the first and second images 152, 154 were formed using respectively different values of the same parameter, the value used in creating the first image being better suited to the device region 148 than the tissue region 150, the value used in creating the second image being better suited to the tissue region than the device region.

Figure 2:
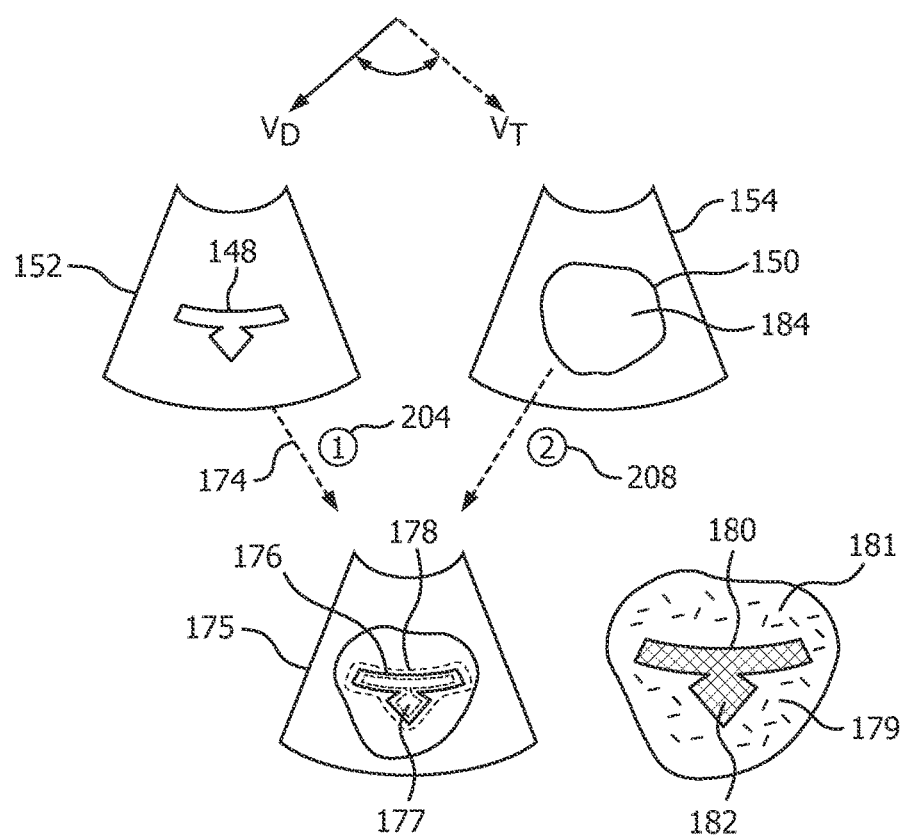
FIG. 2 is a conceptual diagram of an image combination embodiment alternative to that shown in FIG. 1.

In some embodiments, the first and second images 152, 154 are combined by overlaying one onto the other. FIG. 1 shows, by an ordering 171, 172 of operations, the second image 154 serving as the underlying image. In particular, the first image 152 can be overlaid onto the second image 154 as follows. The device region 148 of the first image 152 is segmented out from the first image, and the segmented out portion is registered with the second image 154. Alternatively, the first and second images 152, 154 could be co-registered, and the segmented out portion overlaid in accordance with the registration. Segmentation is based on the known shapes of the mitral valve clip in its different configurations, potentially ranging between wings-extended and wings-unextended, and its known composition. See, e.g., U.S. Pat. No. 8,858,436 to Pagoulatos et al., column 12, lines 30-47, this passage being incorporated herein by reference. The first and second images 152, 154 may have been acquired almost concurrently with the same imaging apertures, in which case registration may occur in place. Alternatively, the two images 152, 154 could be acquired in a manner that is time-gated to a body cycle, such as heartbeat and/or respiration. If the first and second images 152, 154 were acquired from different angles by respective probes in a fixed arrangement, or by separate acoustic windows of a LATTE, co-registration is effected by a transformation between respective image spaces. The segmented portion is then overlaid 174 onto the second image 154 to form the exemplary combination 175 shown. There exists, in the combination 175, between the intervention device and the tissue, a border 176, and inside and outside the border, respective neighborhoods 177, 178, such that the inside neighborhood is part of the first image 152 and such that the outside neighborhood is part of the second image 154. In some embodiments, the combination 175 has a portion 179 outside its depiction 180 of the intervention device, that portion having a color 181, that depiction of the intervention device being in a different color 182. Thus, the shape and position of the device can be precisely shown. Alternatively, as seen in FIG. 2 from an ordering of operations 204, 208, the first image 152 serves as the underlying image. Thus, the second image 154 is overlaid onto the first image 152. This is done by segmenting out the tissue region 150 from the second image 154 and superimposing the segmented out portion onto the first image 152. For either type of overlaying, the edge enhancement 157 is applicable after scan conversion, to make the edges of the device region 148 cleaner. Also, for either type of overlaying, the intervention device 137 depicted in the combination 175 may be immediately surrounded by body tissue depicted in the second image 154 as immediately surrounding the intervention device. Accordingly, a portion 184 of the second image 154 immediately surrounds the device region 148 and, in the combination 175, the immediately surrounding portion resides within the outside neighborhood 178 and immediately surrounds the intervention device 137.

However, it is within the intended scope of what is proposed herein that the combining of the first and second images 152, 154 not be confined to overlaying. The combining could entail alpha blending. In another variation, the device region may be excised from the second image 154 to yield a device-less image and then the segmented device region from the first image 152 can serve as a replacement device region in the second image. As another alternative, an embodiment acquiring the imaging from two different angles can utilize spatial compounding to combine the two images 152, 154. An example of spatial compounding is disclosed in commonly-owned U.S. Pat. No. 7,537,567 to Jago et al., the entire disclosure of which is incorporated herein by reference.

Figure 3:
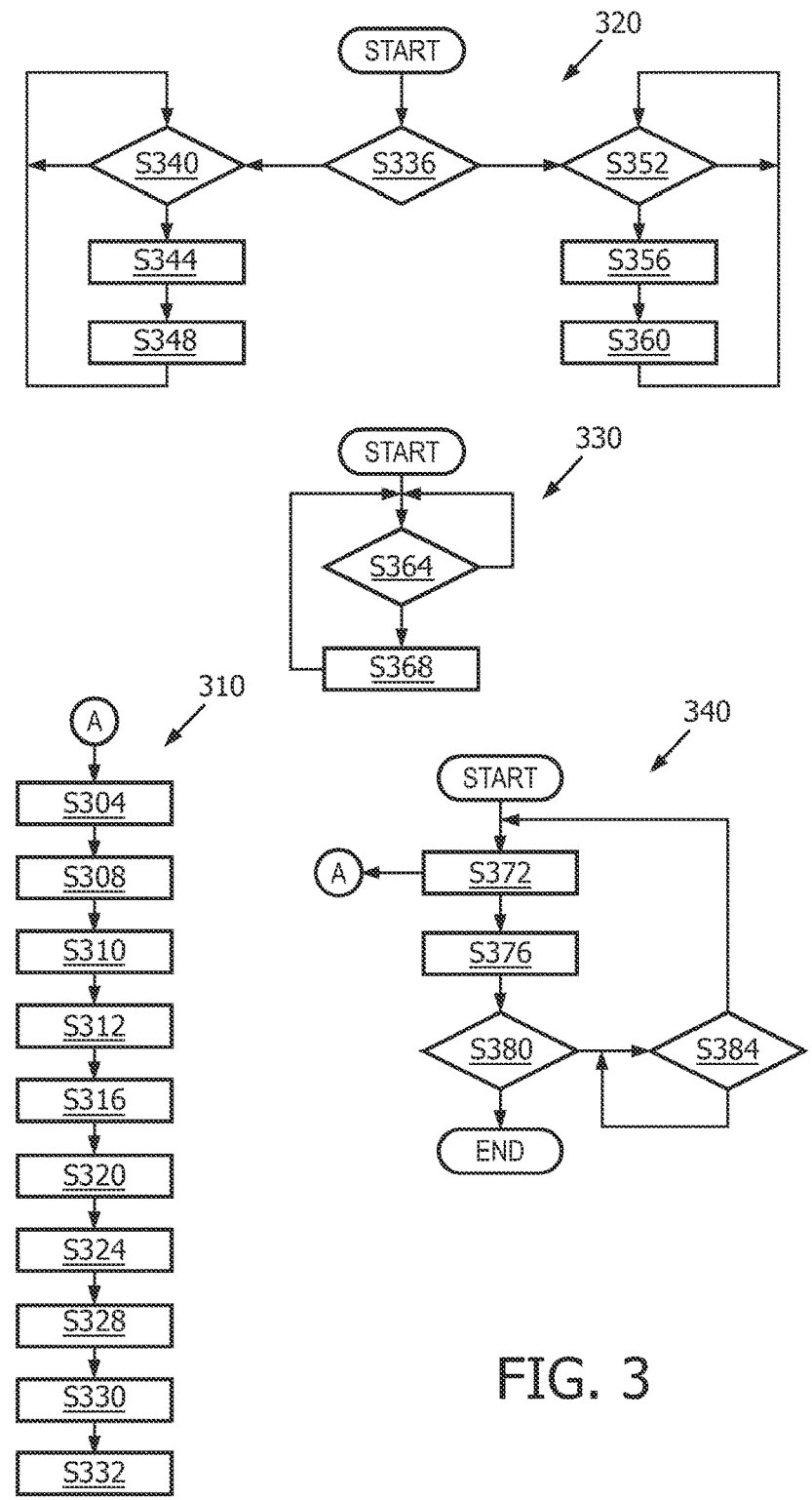
FIG. 3 is a group of flowcharts showing a possible realization of region-specific imaging for overall visual enhancement in accordance with the present invention.

Operationally in one example of region-specific imaging for overall visual enhancement, and with reference to FIG. 3, a pipeline procedure 310 is executed. In particular, a first mode, corresponding to the first or the second preset 158, 164, is selected (step S304). Then, stages 144 of the pipeline 141 are executed in, for example, the following order: pulse-echo, or transmissive, acquisition (step S308); beamforming (step S310); post-processing (step S312); and image processing (step S316). The second mode, corresponding to the other of the first and second preset 158, 164, is selected (step S320). Then imaging acquisition, beamforming, post-processing, and image processing are repeated (steps S324, S328, S330, S332).

Concurrently, an image combination procedure 320 is executed. It is initially set according to whether overlaying is onto the first image 152 or onto the second image 154 (step S336). In particular, if overlaying is onto the second image 154 (step S336), when a pair of first and second images 152, 154 are made available from the pipeline procedure 310 (step S340), the device region 148 is segmented out (step S344). The segmented out region is overlaid onto the second image 154 (step S348), and return is made to the pair availability step S340. If, on the other hand, overlaying is onto the first image 152 (step S336), when a pair of first and second images 152, 154 are made available from the pipeline procedure 310 (step S352), the tissue region 150 is segmented out (step S356). The segmented out region is overlaid onto the first image 152 (step S360), and return is made to the pair availability step S352.

Also concurrently, a display procedure 330 is executed. When a combination becomes available from the overlaying in the combination procedure 320 (step S364), the combination is displayed on the display 112 (step S368).

Also concurrently, a control procedure 340 is executed. The pipeline procedure 310 is invoked (step S372). A pair of first and second images 152, 154 from the pipeline procedure 310 is made available to the combination procedure 320 (step S376). If display of the imaging is to continue (step S380) and when the system is ready to acquire a new image pair (step S384), return is made to the pipeline invoking step S372.

The dynamic nature of the imaging being displayed can advantageously be used in guiding the internal movement of an interventional device 137, as with ultrasound.

Optionally, while retaining that dynamic nature, ones or all of the concurrent procedures 310-340 can be consolidated to result in fewer procedures or a single procedure.

As an alternative to the above-described dynamic, or real time, imaging, the parameter suited to one of the device region 148 and the tissue region 150 in comparison to the other in creating an image may be supplied by the user. For example, the user can interactively operate the user controls 110, e.g., turning a knob or sliding a slide bar, while viewing the image displayed. This can be done for creating, for instance, one of the first image and the second image 152, 154. That image is created using a parameter value determined based on the extent or manner of actuation of the user control. A parameter value more suited to one of the two regions 148, 150 is therefore used to yield respectively the first or second image 152, 154, this use occurring in a stage 144 prior to image processing 156 conducted on a scan-converted image 146 if such image processing is employed. The imaging parameter values 162, 166 by which the medical imaging acquisition unit 118 and the medical imaging post-processing unit 120 carry out imaging acquisition and/or post-processing are adjustable by user operation of the controls 110.

Although the above discussion is in the context of ultrasound, the parameter value, such as a window-level value, suited to the device or tissue can pertain to another medical imaging modality Also, what is proposed herein applies to in vivo, ex vivo, or in vitro examination.

Depiction, within a single imaging modality, of an intervention device and body tissue surrounding the device, is improved by interrogating a subject that includes the intervention device and the tissue. An image is created using, for a parameter, a value, of the parameter, better suited to one or the other of a device region depicting the intervention device and a tissue region depicting the tissue. The value is used to yield respectively either a first image or a second image. Respective presets may correspondingly have different values for the parameter. From jointly the first image and the second image which are both of the single modality, a combination is formed that is an image of the intervention device depicted as surrounded by the tissue. The combinations may be formed dynamically and ongoingly. An apparatus for the improved depiction may be configured for the use of the parameter in a stage prior to image processing conducted on a scan-converted image if such image processing is employed.

It should be noted that the above-mentioned embodiments illustrate rather than limit the invention, and that those skilled in the art will be able to design many alternative embodiments without departing from the scope of the appended claims.

For example, the first and second images and the combination may all be two-dimensional or three-dimensional.

In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer having a computer readable storage medium and/or by means of an integrated circuit having a machine-accessible storage medium. A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM. The mere fact that certain measures are recited in mutually different dependent claims does not indicate that a combination of these measures cannot be used to advantage.

What is claimed is:

1. An imaging apparatus configured for imaging an intervention device and body tissue surrounding said device using a single imaging modality, said apparatus comprising:
   image acquisition and formation circuitry configured to generate a plurality of first images and a plurality of second images of a target area of a subject from a single imaging modality,
   wherein the plurality of first images and the plurality of second images are each generated by imaging from different acoustic windows,
   wherein individual images of the plurality of first images and individual images of the plurality of second images are generated in an alternating manner,
   wherein the plurality of first images are obtained using one or more first parameter values specific for imaging an interventional device in the target area,
   wherein the plurality of second images are obtained using one or more second parameter values specific for imaging tissue within the target area such that the image acquisition circuitry toggles back and forth between using the one or more first parameter values and the one or more second parameter values; and
   image combination circuitry configured for forming a plurality of combined images of the interventional device surrounded by the tissue using the individual images of the plurality of first images and the individual ones of the plurality of second images, wherein forming comprises:
      segmenting at least a portion of the individual ones of the plurality of first images, the segmented portion includes the interventional device and its surrounding boundary area; and
      overlapping the segmented portion onto the individual ones of the plurality of second images to form the plurality of combined images, the plurality of combined images comprising the tissue, the interventional device, and the boundary area.

2. The apparatus of claim 1, wherein at least one first parameter value and at least one second parameter value correspond to the same parameter.

3. The apparatus of claim 1, wherein the first and second parameter values are different.

4. The apparatus of claim 1, wherein at least one first parameter value and at least one second parameter value correspond to different parameters.

5. The apparatus of claim 1, wherein the boundary area is a different color than the interventional device.

6. The apparatus of claim 1, wherein said forming further comprises applying edge enhancement to a depiction of said intervention device.

7. The apparatus of claim 1, wherein the first and second parameter values comprise values of image acquisition parameters.

8. The apparatus of claim 1, wherein the first and second parameter values comprise values of post-processing parameters.

9. The apparatus of claim 1, said intervention device including at least one of metal and a mitral valve clip.

10. The apparatus of claim 1, wherein said plurality of first images and the plurality of second images are each generated by imaging from different particular spatial directions.

11. An imaging method for imaging an intervention device and body tissue surrounding said device using a single imaging modality, said method comprising:
- generating a plurality of first images and a plurality of second images of a target area of a subject from a single imaging modality,
- wherein individual images of the plurality of first images and individual images of the plurality of second images are generated in an alternating manner,
- wherein said plurality of first images and the plurality of second images are each generated by imaging from different acoustic windows,
- wherein the plurality of first images are obtained using one or more first parameter values specific for imaging an interventional device in the target area,
- wherein the plurality of second images are obtained using one or more second parameter values specific for imaging tissue within the target area,
- wherein parameter values used toggle between the one or more first parameter values and the one or more second parameter values; and
- forming a plurality of combined images of the interventional device surrounded by the tissue using the individual images of the plurality of first images and the individual images of the plurality of second images, wherein forming comprises:
- segmenting at least a portion of the individual images of the plurality of first images, the segmented portion includes the interventional device and its surrounding boundary area; and
- overlapping the segmented portion onto the individual images of the plurality of second image to form the plurality of combined images, the plurality of combined images comprising the tissue, the interventional device, and the boundary area.

12. The method of claim 11, wherein at least one first parameter value and at least one second parameter value correspond to the same parameter.

13. The method of claim 11, wherein the first and second parameter values are different.

14. The method of claim 11, wherein at least one first parameter value and at least one second parameter value correspond to different parameters.

15. The method of claim 11, wherein the boundary area is a different color than the interventional device.

16. The apparatus of claim 1, wherein the first parameter or the second parameter is selected from a group comprising a central frequency, a mechanical index, and an analog gain.

17. The apparatus of claim 1, wherein the first parameter or the second parameter is selected from a group comprising a digital gain, a gamma correction, and an intensity based thresholding.

18. The apparatus of claim 1, wherein the different acoustic windows are provided by separate probes coupled to the apparatus, wherein a first probe provides a first acoustic window for generating the plurality of first images and a second probe provides a second acoustic window for generating the plurality of second images.

19. The apparatus of claim 1, wherein the different acoustic windows are provided by a single probe having a large surface area coupled to the apparatus, wherein a first portion of the large surface area provides a first acoustic window for generating the plurality of first images and a second portion of the large surface area provides a second acoustic window for generating the plurality of second images.

20. The apparatus of claim 1, wherein the different acoustic windows are provided by a single probe coupled to the apparatus, wherein the single probe is placed in a first position for generating the plurality of first images and the single probe is placed in a second position for generating the plurality of second images.

* * * * *